United States Patent [19]

Iizuka et al.

[11] Patent Number: 4,461,905
[45] Date of Patent: Jul. 24, 1984

[54] IMIDAZOLE DERIVATIVES

[75] Inventors: Kinji Iizuka; Tetsuhide Kamijo; Ryoji Yamamoto; Hiromu Harada, all of Nagano, Japan

[73] Assignee: Ono Pharmaceutical Co., Ltd., Osaka, Japan

[21] Appl. No.: 413,204

[22] Filed: Aug. 30, 1982

[30] Foreign Application Priority Data

Aug. 29, 1981 [JP] Japan ................. 56-135892

[51] Int. Cl.³ .......................................... C07D 233/60
[52] U.S. Cl. .................................................. 548/341
[58] Field of Search ........................ 548/341; 542/413

[56] References Cited

U.S. PATENT DOCUMENTS 4,298,603 11/1981 Chang et al. ................. 548/341 X
4,366,036 12/1982 Lash et al. ..................... 548/341 X

OTHER PUBLICATIONS

Grimmett, *Adv. Heterocycl. Chem.* 12, 162-167 (1970).
Haring, M., *Helv. Chim. Acta.*, XLII, 1845 (1959).
Baggaley, K., *J. Med. Chem.*, 18(8), 833 (1975).
Walker, K. et al., *J. Med. Chem.*, 24, 67 (1981).
Nardi, D. et al., *J. Med. Chem.*, 24, 727 (1981).
Godefroi, E. et al., *J. Med. Chem.*, 12, 784 (1969).
Kikugawa, Y., *Synthesis*, p. 124 (1981).
Yamauchi, K., *J.C.S. Perkin I,* 2506 (1973).
Loozen, H. et al., *J. Org. Chem.,* 40(22), 3279 (1975).
*Chemical Abstracts,* 86:155649t (1977) [JPN. Kokai 76, 105,060, 9/17/76].
Godefroi, E. et al., *Rec. Trav. Chem.*, 93, 56 (1974).
Olofson, R. et al., *J. Org. Chem.,* 35(7), 2246 (1970).
Boyer, J., *J. Am. Chem. Soc.,* 74, 6274 (1952).
Staab, H., *Angew. Chem. Internat. Edit.,* 1(7), 351 (1962).
Birkofer, L. et al., *Chem. Ber.,* 93, 2804 (1960).
Curtis, N. et al., *J. Org. Chem.,* 45, 4038 (1980).
van der Eijk, J. et al., *J. Org. Chem.,* 45, 547 (1980).
Iizuka, K. et al., *J. Med. Chem.,* 24, 1139 (1981).
Kamijo, T. et al., *Chem. Pharm. Bull.,* 31(4), 1213 (1983).

McOmie, J., (Editor), *Protective Groups in Organic Chemistry,* Plenum Press, London, 1973, p. 49.

Primary Examiner—Richard A. Schwartz
Attorney, Agent, or Firm—Sughrue, Mion, Zinn, Macpeak and Seas

[57] ABSTRACT

The imidazole derivatives of the general formula:

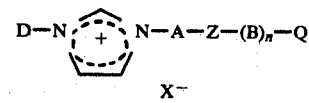

wherein A and B may be the same or different, and each is a straight- or branched-chain alkylene or alkenylene group having 1 to 8 carbon atoms, D is an acyl group having 2 to 10 carbon atoms, an alkoxycarbonyl group having 2 to 7 carbon atoms or a dialkoxymethyl group having 3 to 13 carbon atoms, Q is a cyano group or an alkoxycarbonyl group having 2 to 7 carbon atoms, X is a halogen atom, Z is

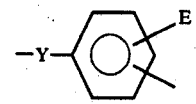

(wherein E is a hydrogen atom, a halogen atom, an alkyl group having 1 to 6 carbon atoms or an alkoxy group having 1 to 6 carbon atoms, Y is an oxygen atom or a sulfur atom and may be connected with either A or B), n is zero or 1, with the proviso that n is 1 when Y connects with B.

These compounds are novel compounds and are useful as intermediates in producing 1-substituted imidazole derivatives which possess strong and specific inhibitory effects on thromboxane synthetase and thus are useful as therapeutically active agents for treatment of diseases caused by thromboxane $A_2$.

19 Claims, No Drawings

IMIDAZOLE DERIVATIVES

FIELD OF THE INVENTION

This invention relates to novel imidazole derivatives and to a process for their preparation. More particularly, this invention relates to 1,3-disubstituted imidazole derivatives useful as intermediates in producing 1-substituted imidazole derivatives which exhibit strong and specific inhibitory effects on thromboxane synthetase and thus are useful as therapeutically active agents for treatment of diseases caused by thromboxane $A_2$.

BACKGROUND OF THE INVENTION

The imidazole derivatives of the general formula (V):

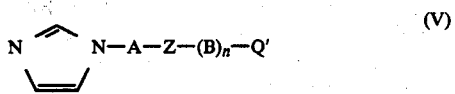

(V)

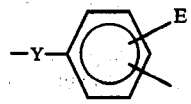

wherein A and B may be the same or different, and each is a straight- or branched-chain alkylene or alkenylene group having 1 to 8 carbon atoms, Q' is a carboxyl group or an alkoxycarbonyl group, Z is

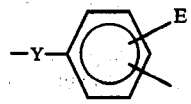

(wherein E is a hydrogen atom, a halogen atom, an alkyl group having 1 to 6 carbon atoms, Y is an oxygen atom or a sulfur atom and may be connected with either A or B), n is zero or 1, with the proviso that n is 1 when Y connects with B; are known to exhibit strong and specific inhibitory effects on thromboxane synthetase and thus are useful as therapeutical agents for treatment of diseases caused by thromboxane $A_2$, as reported in the British patent publication Nos. 2 038 821 A, 2 041 363 A, and 2 031 408 A. Furthermore, several methods for producing said derivatives have been also disclosed in the above British patent publications.

Any of the methods disclosed in said British patent publications comprises a process of N-alkylation of an imidazole ring with a halide compound in the procedure of synthesis of said imidazole derivatives, and therefore, there is a problem in these conventional methods that di-N-alkylation can be occured and an imidazolium compound is produced as a by-product in a large amount. Such by-product adversely affects the yield and purity of the desired product.

Accordingly, it is an object of this invention to provide 1,3-disubstituted imidazole derivatives having the general formula (I) below which are useful as intermediates in the production of the imidazole derivatives of the general formula (V) above.

It is another object of this invention to provide a process for producing 1,3-disubstituted imidazole derivatives (I).

It is still another object of this invention to provide a new process for producing the imidazole derivatives of the general formula (V) above, which is superior to prior art methods such as those described in the above British patent publications.

Other objects and advantages of this invention will become apparent from the following description and examples.

DESCRIPTION OF THE INVENTION

This invention provides 1,3-disubstituted imidazole derivatives of the general formula (I):

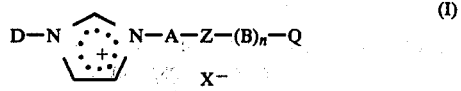

(I)

wherein A and B may be the same or different, and each is a straight- or branched-chain alkylene or alkenylene group having 1 to 8 carbon atoms, D is an acyl group having 2 to 10 carbon atoms, an alkoxycarbonyl group having 2 to 7 carbon atoms or an dialkoxymethyl group having 3 to 13 carbon atoms, Q is a cyano group or an alkoxycarbonyl group having 2 to 7 carbon atoms, X is a halogen atom, Z is

(wherein E is a hydrogen atom, a halogen atom, an alkyl group having 1 to 6 carbon atoms or an alkoxy group having 1 to 6 carbon atoms, Y is an oxygen atom or a sulfur atom and may be connected with either A or B), n is zero or 1, with the proviso that n is 1 when Y connects with B; which are intermediates for producing the imidazole derivatives of the general formula (V) above which possess strong and specific inhibitory effects on thromboxane synthetase and thus are useful as therapeutical agents for treatment of diseases caused by thromboxane $A_2$.

The compounds of the general formula (I) of the present invention include the compounds of the formula (Ia):

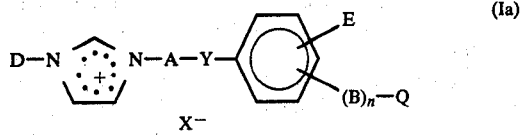

(Ia)

wherein D, A, Y, B, Q, n, E and X are as previously defined and the compounds of the formula (Ib):

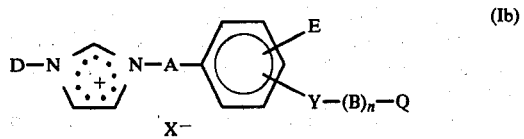

(Ib)

wherein D, A, Y, B, Q, n, E and X are as previously defined and n is 1.

The compounds of the general formula (I) of this invention can be prepared by reacting a compound of the general formula (II):

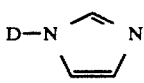

$$D-N\underset{\underline{\qquad}}{\frown}N \qquad (II)$$

wherein D is as previously defined, with a compound of the general formula (III):

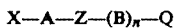

X—A—Z—(B)ₙ—Q    (III)

wherein X, A, Z, B, Q and n are as previously defined.

The compounds corresponding to the general formula (II) which are employed as a starting material are known compounds, and can be prepared according to the methods of synthesis described in chemical literatures such as J. Amer. Chem. Soc. 74, 6274 (1952), J. Org. Chem. 45, 4038 (1980), Angew. Chem. Int. Ed. Engl. 1, 351 (1962), Chem. Ber. 93, 2804 (1960). Examples of said compounds include 1-acetylimidazole, 1-propionylimidazole, 1-benzoylimidazole, 1-ethoxycarbonylimidazole, 1-diethoxymethylimidazole. The more preferred compounds are 1-acetylimidazole and 1-benzoylimidazole and the most preferred compound is 1-acetylimidazole.

The compounds of the general formula (III) used as a starting material are also known compounds, and can be prepared according to the methods described in chemical literatures such as J. Chem. Soc. 103 (1942), J. Med. Chem. 7(4), 511 (1964), J. Med. Chem. 8(3), 356 (1965), J. Med. Chem. 14(9), 836 (1971), Chem. Abstr. 71, p21898e (1969). Examples of said compounds include lower alkyl esters of 2-, 3- or 4-chloromethylphenoxyacetic acid, 2-, 3- or 4-bromomethylphenoxyacetic acid, 2-, 3- or 4-iodomethylphenoxyacetic acid, 2-(2-, 3- or 4-chloromethylphenoxy)propionic acid, 2-(2-, 3- or 4-bromomethylphenoxy)propionic acid, 2-(2-, 3- or 4-iodomethylphenoxy)propionic acid, 2-(2-, 3- or 4-chloromethylphenoxy)isobutyic acid, 2-(2-, 3- or 4-bromomethylphenoxy)isobutyric acid, 2-(2-, 3- or 4-iodomethylphenoxy)-isobutyric acid, 2-(2-, 3- or 4-chloromethylphenylthio)-isobutyric acid, 2-(2-, 3- or 4-bromomethylphenylthio)-isobutyric acid, 2-(2-, 3- or 4-iodomethylphenylthio)-isobutyric acid, 4-chloro-2-chloromethylphenoxyacetic acid, 4-chloro-2-bromomethylphenoxyacetic acid, B 4-chloro-2-iodomethylphenoxyacetic acid, 2-methoxy-4-chloromethylphenoxyacetic acid, 2-methoxy-4-bromomethylphenoxyacetic acid, 2-methoxy-4-iodomethylphenoxyacetic acid, 2-, 3- or 4-(2-bromoethoxy)benzoic acid, 2-, 3- or 4-(2-iodoethoxy)benzoic acid, 2-, 3- or 4-(2-p-toluenesulfonyloxyethoxy)benzoic acid, 4-(2-bromoethoxy)cinnamonitrile, 4-(2-iodoethoxy)-cinnamic acid, 4-(2-p-toluenesulfonyloxyethoxy)cinnamic acid, 3-[4-(2-bromoethoxy)-phenyl]propionic acid, 3-[4-(2-iodoethoxy)phenyl]propionic acid, 3-[4-(2-p-toluenesulfonyloxyethoxy)-phenyl]propionic acid, 4-(3-bromopropoxy)benzoic acid, 4-(3-iodopropoxy)benzoic acid, 4-(3-p-toluenesulfonyloxypropoxy)benzoic acid, etc and the corresponding nitrile compounds of these acid compounds.

The compounds of the general formula (I) of this invention can be easily prepared by the following procedure: A compound of the general formula (II) is reacted with a compound of the general formula (III) for a period of from about 30 minutes to overnight (about 10–20 hours) at from room temperature (about 20°–30° C.) to about 120° C. under stirring in the absence of or in the presence of an inert organic solvent such as chloroform, methylene chloride, benzene, toluene, acetonitrile, preferably acetonitrile. After completion of the reaction, an adequate amount of an organic solvent such as diethyl ether is added to the reaction mixture or, if necessary, to the residue obtained after evaporating the reaction mixture, and the precipitated crystals or crystalline powders are collected by filtration and dried to give the desired compound of the general formula (I).

The compounds of the general formula (I) of this invention are novel compounds not previously desclosed in literatures. Examples of the compounds of the general formula (I) include 1-acetyl-3-(2-ethoxycarbonylmethoxybenzyl)imidazolium bromide, 1-acetyl-3-(4-ethoxycarbonylmethoxybenzyl)imidazolium bromide, 1-acetyl-3-(4-cyanomethoxybenzyl)imidazolium iodide, 1-acetyl-3-[4-(1-ethoxycarbonylethoxy)benzyl]imidazolium bromide, 1-acetyl-3-[4-(1-ethoxycarbonyl-1-methylethoxy)-benzyl]imidazolium bromide, 1-acetyl-3-(2-ethoxycarbonylmethoxy-5-chlorobenzylimidazolium bromide, 1-acetyl-3-(3-methoxy-4-ethoxycarbonylmethoxybenzyl)imidazolium iodide, 1-acetyl-3-[4-(1-ethoxycarbonyl-1-methylethylthio)benzyl]imidazolium bromide, 1-acetyl-3-[2-(4-ethoxycarbonylphenoxy)ethyl]-imidazolium iodide, 1-acetyl-3-[2-(4-cyanophenoxy)ethyl]-imidazolium iodide 1-acetyl-3-[3-(4-ethoxycarbonylphenoxy)-propyl]imidazolium iodide, 1-benzoyl-3-[4-(1-ethoxycarbnoyl-1-methylethoxy)benzyl]imidazolium bromide, 1-ethoxycarbonyl-3-(4-ethoxycarbonylmethoxybenzyl)imidazolium iodide and the like.

In accordance with the present invention process, the problem associated with the procedures disclosed in the above British patent publications, i.e. formation of an imidazolium compound as a by-product, is eliminated, and furthermore, as the reaction can be carried out under a neutral condition and the reaction condition is mild, the formation of by-product is little and the desired product (I) can be obtained in good yield with high purity.

The compounds of the general formula (I) of this invention can be easily converted in good yield into the imidazole derivatives of the general formula (V). That is, the imidazole derivatives of the general formula (V) can be obtained by treating an aqueous solution of the compounds of the general formula (I) with an acidic or a basic compound, for example, inorganic acid such as hydrochloric acid, hydrobromic acid, sulfuric acid phosphoric acid and the like, or organic and inorganic acid base such as sodium hydroxide, potassium hydroxide, sodium carbonate, potassium carbonate, sodium bicarbonate, potassium bicarbonate, methylamine, ethylamine, dimethylamine, diethylamine, trimethylamine, triethylamine, piperidine, pyrrolidine, morpholine and the like.

Thus, in accordance with the present invention process, as a further advantage, the imidazole derivatives of the general formula (V) above, can be easily obtained in high yield and purity.

Accordingly, the compounds of the general formula (I) of this invention are important intermediates in producing the imidazole derivatives of the general formula (V) above which possess strong and specific inhibitory effects on thromboxane synthetase and thus are useful as therapeutical agents for treatment of dieseases caused by thromboxane A₂, and the process of this invention is advantageous in the production of the imidazole derivatives of the general formula (V) above on an industrial scale, which is superior to prior art methods such as that described in the British Patent publication Nos. 2 038 821 A, 2 041 363 A and 2 031 408 A.

This invention is further illustrated in more detail by the following examples wherein the melting point of the product obtained is uncorrected.

EXAMPLE 1

2.2 g of 1-acetylimidazole and 5.46 g of ethyl 4-bromomethylphenoxyacetate were added to 5 ml of dry acetonitrile, and the mixture was heated at 60° C. for 2 hours. After completion of the reaction, the solvent was evaporated under reduced pressure. The residue was triturated with an adequate amount of dry diethyl ether and the resulting powder was collected by filtration and dried to obtain 7.5 g of 1-acetyl-3-[4-(ethoxycarbonylmethoxy)benzyl]imidazolium bromide. (98.6% yield). Colorless hygroscopic amorphous.

IR absorption spectrum (KBr)
$\nu$CO: 1770, 1745 cm$^{-1}$
NMR spectrum (d$_6$-DMSO)
δ: 1.20(t, 3H, J=7 Hz), 1.92 (s, 3H), 4.20 (q, 2H, =7 Hz), 4.82(s, 2H), 5.45(s, 2H), 7.00(d, 2H, J=9 Hz), 7.48(d,2H, J=9Hz), 7.73 (m, 1H), 7.85(m, 1H), 9.40(m, 1H).

EXAMPLE 2

1.7 g of 1-benzoylimidazole and 3.0 g of ethyl 4-bromomethylphenoxyisobutylate were added to 5 ml of dry acetonitrile, and the mixture was stirred at room temperature overnight. After completion of the reaction, an adequate amount of dry diethyl ether is added to the reaction mixture. The precipitated powder was collected by filtration and dried to obtain 4.7 g of 1-benzoyl-3-[4-(1-ethoxycarbonyl-1-methylethoxy)benzyl]imidazolium bromide (quantitative yield). Colerless hygroscopic amorphous.

IR absorption spectrum (KBr)
$\nu$CO: 1780, 1730 cm$^{-1}$
NMR spectrum (d$_6$-DMSO)
δ: 1.13(t, 3H, J=7 Hz), 1.50(s, 6H), 4.15(q, 2H, J=7 Hz), 5.42(s, 2H), 6.80(d, 2H, J=8 Hz), 7.12-8.02(m, 9H), 9.29(m, 1H).

EXAMPLE 3

2.2 g of 1-acetylimidazole, 5.5 g of ethyl 4-(2-bromoethoxy)benzoate, and 3.0 g of sodium iodide were added to 10 ml of dry acetonitrile, and the mixture was heated in a sealed tube under nitrogen atmosphere at 100° C. for 6 hours. After the reaction mixture was cooled, the insoluble materials were filtered off and the filtrate was concentrated under reduced pressure. The residue was triturated with an adequate amount of dry diethyl ether and the r resulting powder was collected by filtration and dried to obtain 6.2 g of 1-acetyl-3-[2-(4-ethoxycarbonylphenoxy)-ethyl]imidazolium iodide (72% yield). Colorless hygroscopic amorphous.

IR absorption spectrum (KBr)
$\nu$CO: 1780, 1705 cm$^{-1}$
NMR spectrum (d$_6$-DMSO)
δ: 1.30(t,3H, J=7 Hz), 1.90(s,3H), 4.30(q, 2H, J=7 Hz), 4.10-4.76(m,4H), 7.07(d,2H, J=9 Hz), 7.45(m, 1H), 7.67(m, 1H), 7.92(d, 2H, J=9 Hz), 8.73(m, 1H).

EXAMPLE 4

1.4 g of 1-ethoxycarbonylimidazole, 2.5 g of ethyl 4-chloromethylphenoxyacetate and 1.7 g of sodium iodide were added to 5 ml of dry acetonitrile, and the mixture was stirred at room temperature for 6 hours. After completion of the reaction, the insoluble materials were filtered off and the filtrate was concentrated under reduced pressure. The residue was triturated with an adequate amount of dry diethyl ether, the resulting powder was collected by filtration and dried to obtain 4.6 g of 1-ethoxycarbonyl-3-(4-ethoxycarbonylmethoxybenzyl)imidazolium iodide (quantitative yield). Colorless hygroscopic amorphous.

IR absorption spectrum (KBr)
$\nu$CO: 1795, 1750 cm$^{-1}$
NMR spectrum (d$_6$-DMSO)
δ: 1.13(t, 3H, J=7 Hz), 1.35(t, 3H, J=7 Hz), 4.15 (q, 2H, J=7 Hz), 4.53(q, 2H, J=7 Hz), 4.77(s, 2H), 5.48(s, 2H), 6.96(d, 2H, J=8 Hz), 7.49(d, 2H, J=8 Hz), 7.94(m, 1H), 8.10(m, 1H), 10.09(m, 1H).

EXAMPLE 5

By using the same procedure as described in Examples 1 to 4, the following compounds were obtained.

(1) 1-acetyl-3-(2-ethoxycarbonylmethoxybenzyl)imidazolium bromide. Colorless hygroscopic amorphous.

IR absorption spectrum (KBr)
$\nu$CO: 1780, 1745 cm$^{-1}$
NMR spectrum (d$_6$-DMSO)
δ: 1.20(t, 3H, J=7 Hz), 1.90(s, 3H), 4.20(q, 2H, J=7 Hz), 4.90(s, 2H), 5.44(s, 2H), 6.90-7.60 (m, 4H), 7.65(m, 1H), 7.76(m,1H), 9.18(m, 1H).

(2) 1-acetyl-3-(4-cyanomethoxybenzyl)imidazolium iodide. Colorless needles. m.p. 169°-170° C. (acetonitrile)

IR absorption spectrum (KBr)
$\nu$CO: 1780 cm$^{-1}$
NMR spectrum (d$_6$-DMSO)
δ: 1.92(s, 3H), 5.20(s, 2H), 5.32(s, 2H), 7.11(d, 2H, J=9 Hz), 7.35(m, 1H), 7.42(d, 2H, J=9 Hz), 7.53(m, 1H), 8.61(m, 1H).

(3) 1-acetyl-3-[4-(1-ethoxycarbonylethoxy)benzyl]imidazolium bromide. Colorless hygroscopic amorphous.

IR absorption spectrum (KBr)
$\nu$CO: 1775, 1740 cm$^{-1}$
NMR spectrum (d$_6$-DMSO)
δ: 1.15(t, 3H, J=7 Hz), 1.50(d, 3H, J=7 Hz), 1.90(s, 3H), 4.15(q, 2H, J=7 Hz), 4.98(q, 1H, J=7 Hz), 5.40(s, 2H), 6.93(d, 2H, J=9 Hz), 7.45(d, 2H, J=9 Hz), 7.70(m, 1H), 7.80(m, 1H), 9.31(m, 1H).

(4) 1-acetyl-3-[4-(1-ethoxycarbonyl-1-methylethoxy)benzyl]imidazolium bromide. Colorless hygroscopic amorphous.

IR absorption spectrum (KBr)
$\nu$CO: 1780, 1730 cm$^{-1}$
NMR spectrum (d$_6$-DMSO)
δ: 1.15(t, 3H, J=7 Hz), 1.54(s, 6H), 1.90(s, 3H), 4.18(q, 2H, J=7 Hz), 5.45(s, 2H), 6.80(d, 2H, J=9 Hz), 7.38(d, 2H, J=9 Hz), 7.70(m, 1H), 7.80(m, 1H), 9.28(m, 1H).

(5) 1-acetyl-3-[4-(1-ethoxycarbonyl-1-methylethylthio)benzyl]imidazolium bromide. Colorless hygroscopic amorphous.

IR absorption spectrum (KBr)
$\nu$CO: 1785, 1710 cm$^{-1}$
NMR spectrum (d$_6$-DMSO)
δ: 1.10(t, 3H, J=7 Hz), 1.40(s, 6H), 1.92(s, 3H), 4.05(q, 2H, J=7 Hz), 5.55 (s, 2H), 7.48(s, 4H), 7.75(m, 1H), 7.87(m, 1H), 9.40(m, 1H).

(6) 1-acetyl-3-(5-chloro-2-ethoxycarbonylmethoxybenzyl)imidazolium bromide. Colorless hygroscopic amorphous.

IR absorption spectrum (KBr)
νCO: 1780, 1745 cm$^{-1}$
NMR spectrum (d$_6$-DMSO)
δ: 1.22(t, 3H, J=7 Hz), 1.92(s, 3H), 4.21(q, 2H, J=7 Hz), 4.96(s, 2H), 5.47(s, 2H), 7.00–7.90(m, 5H), 9.27(m, 1H).

(7) 1-acetyl-3-(4-ethoxycarbonylmethoxy-3-methoxybenzyl)imidazolium iodide. Colorless needles. m.p. 131°–132° C. (acetonitrile)
IR absorption spectrum (KBr)
νCO: 1765, 1745 cm$^{-1}$
NMR spectrum (d$_6$-DMSO)
δ: 1.19(t, 3H, J=7 Hz), 1.92(s, 3H), 3.78(s, 3H), 4.15(q, 2H, J=7 Hz), 4.75(s, 2H), 5.20(s, 2H), 6.70–7.25(m, 4H), 7.40(m, 1H), 8.30(m, 1H).

(8) 1-acetyl-3-[2-(4-cyanophenoxy)ethyl]imidazolium iodide. Colorless hygroscopic amorphous.
IR absorption spectrum (KBr)
νCN: 2240 cm$^{-1}$
νCO: 1770 cm$^{-1}$
NMR spectrum (d$_6$-DMSO)
δ: 1.93(s, 3H), 4.30–4.80(m, 4H), 7.12(d, 2H, J=9 Hz), 7.40(m, 1H), 7.62(m, 1H), 7.78(d, 2H, J=9 Hz), 8.62(m, 1H).

(9) 1-acetyl-3-[3-(4-ethoxycarbonylphenoxy)propyl]imidazolium iodide. Colorless hygroscopic amorphous.
IR absorption spectrum (neat)
νCO: 1780, 1700 cm$^{-1}$
NMR spectrum (d$_6$-DMSO)
δ: 1.32(t, 3H, J=7 Hz), 1.94(s, 3H), 2.20–2.45(m, 2H), 4.00–4.50(m, 6H), 7.05(d, 2H, J=9 Hz), 7.40(m, 1H), 7.60(m, 1H), 7.94(d, 2H, J=9 Hz), 8.60(m, 1H).

REFERENCE EXAMPLE 1

7.5 g of 1-acetyl-3-[4-(ethoxycarbonylmethoxy)benzyl]imidazolium bromide was dissolved in 50 ml of water, and a sodium bicarbonate was added in small portion to the solution to make it slightly basic. The separated oily substance was extracted with chloroform. After the chloroform extract was washed with water and dried over anhydrous magnesium sulfate, and the solvent was evaporated under reduced pressure to obtain 4.3 g of ethyl 4-(1-imidazolylmethyl)phenoxyacetate (83.9% yield). Pale yellow oil.
IR absorption spectrum (neat)
νCO: 1760 cm$^{-1}$
NMR spectrum (CDCl$_3$)
δ: 1.30(t, 3H, J=7 Hz), 4.25(q, 2H, J=7 Hz), 4.55(s, 2H), 5.10(s, 2H), 6.77–7.72(m, 7H).
Elementrary analysis as C$_{14}$H$_{16}$O$_3$N$_2$

|       | C (%) | H (%) | (N %) |
|-------|-------|-------|-------|
| Calcd.| 64.60 | 6.20  | 10.76 |
| Found | 64.55 | 6.31  | 10.60 |

To a solution of 0.42 g of sodium hydroxide in 30 ml of water was added 2.3 g of ethyl 4-(1-imidazolylmethyl)phenoxyacetate and the mixture was stirred at room temperature for 20 minutes. After completion of the reaction, an adequate amount of diluted hydrochloric acid was added to the solution to make it acidic. The reaction mixture was concentrated to dryness under reduced pressure, and the residue was recrystallized from water to obtain 2.4 g of 4-(1-imidazolylmethyl)phenoxyacetic acid hydrochloride monohydrate (94.9% yield). Colorless needles.
m.p. 92°–96° C.
IR absorption spectrum (KBr)
νCO: 1755 cm$^{-1}$
NMR spectrum (d$_6$-DMSO)
δ: 4.67(s, 2H), 5.40(s, 2H), 6.88(d, 2H), 7.38(d, 2H), 7.60(t, 1H), 7.75(t, 1H), 9.45(m, 1H).
Elementrary analysis as C$_{12}$H$_{12}$O$_3$N$_2$.HCl.H$_2$O

|       | C (%) | H (%) | N (%) |
|-------|-------|-------|-------|
| Calcd.| 50.27 | 5.27  | 9.73  |
| Found | 50.16 | 5.22  | 9.85  |

REFERENCE EXAMPLE 2

A mixture of 1.3 g of 1-acetyl-3-[2-(4-ethoxycarbonylphenoxy)ethyl]imidazolium iodide in 100 ml of 2N-hydrochloric acid was heated at 80° C. for 2 hours. After cooling, the solution was treated with an activated charcoal and concentrated under reduced pressure. The residue were triturated with acetone and the resulting crystals were filtered and dried to obtain 0.64 g of 4-[2-(1-imidazolyl)ethoxy]benzoic acid hydrochloride (79.0% yield). Colorless granules.
m.p. 230°–235° C.
IR absorption spectrum (KBr)
νCO: 1675 cm$^{-1}$
NMR spectrum (d$_6$-DMSO)
δ: 4.45–4.65(m,2H), 4.65–4.85(m, 2H), 7.03(d, 2H, J=8 Hz), 7.74(m, 1H), 7.91(d, 2H, J=8 Hz), 7.93(m, 1H), 9.37(m, 1H).
Elementrary analysis as C$_{12}$H$_{12}$O$_3$N$_2$.HCl

|       | C (%) | H (%) | N (%) |
|-------|-------|-------|-------|
| Calcd.| 53.64 | 4.88  | 10.43 |
| Found | 53.55 | 4.68  | 10.16 |

What is claimed is:
1. An imidazole derivative of the following formula:

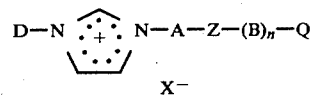

wherein A and B may be the same or different, and each is a straight- or branched-chain alkylene or alkenylene group having 1 to 8 carbon atoms, D is an alkanoyl group having 2 to 10 carbon atoms, an alkoxycarbonyl group having 2 to 7 carbon atoms or a dialkoxymethyl group having 3 to 13 carbon atoms, Q is a cyano group or an alkoxycarbonyl group having 2 to 7 carbon atoms, X is a halogen atom, Z is

(wherein E is a hydrogen atom, a halogen atom, an alkyl group having 1 to 6 carbon atoms or an alkoxy group having 1 to 6 carbon atoms, Y is an oxygen atom or a sulfur atom and may be connected with either A or B), n is zero or 1, with the proviso that n is 1 when Y connects with B.

2. An imidazole derivative as claimed in claim 1 wherein said derivative has the following formula:

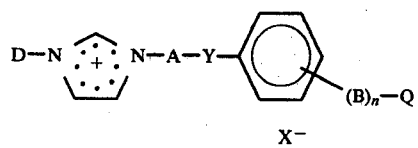

wherein D, A, Y, B, Q, n, and X are as previously defined.

3. An imidazole derivative as claimed in claim 1 wherein said derivative has the following formula:

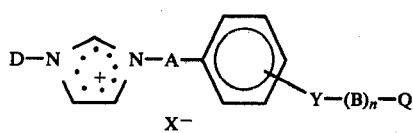

wherein D, A, Y, B, Q, n, and X are as previously defined.

4. An imidazole derivative claimed in claim 2 or claim 3 wherein D is an alkanoyl group having 2 to 10 carbon atoms.

5. An imidazole derivatives claimed in claim 4 wherein D is acetyl group.

6. An imidazole derivative claimed in claim 2 or claim 3 wherein D is benzoyl group.

7. The imidazole derivative claimed in claim 3 of the formula:

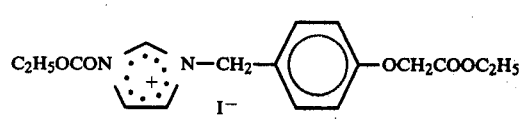

8. The imidazole derivative claimed in claim 5 of the formula:

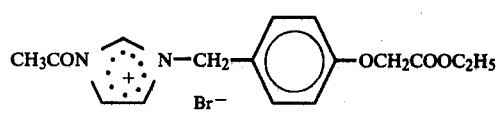

9. The imidazole derivative claimed in claim 5 of the formula:

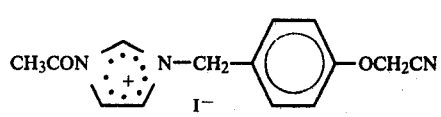

10. The imidazole derivative claimed in claim 5 of the formula:

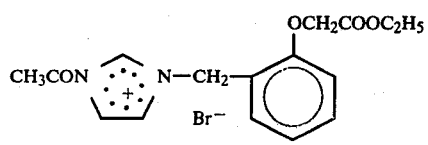

11. The imidazole derivative claimed in claim 5 of the formula:

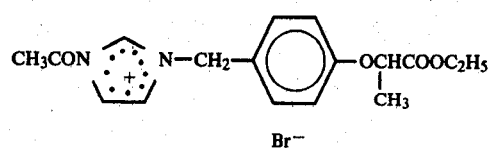

12. The imidazole derivative claimed in claim 5 of the formula:

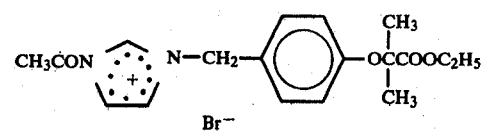

13. The imidazole derivative claimed in claim 5 of the formula:

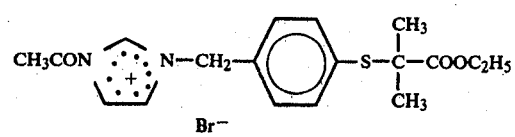

14. The imidazole derivative claimed in claim 5 of the formula:

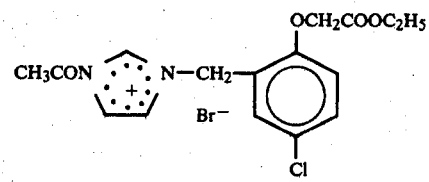

15. The imidazole derivative claimed in claim 5 of the formula:

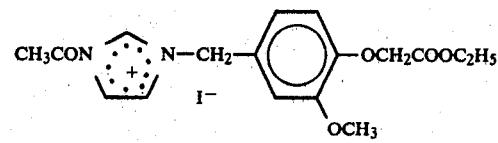

16. The imidazole derivative claimed in claim 6 of the formula:

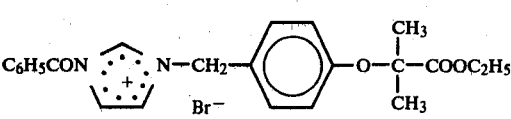

17. The imidazole derivative claimed in claim 5 of the formula:

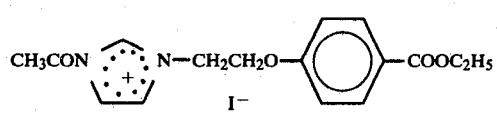

18. The imidazole derivative claimed in claim 5 of the formula:

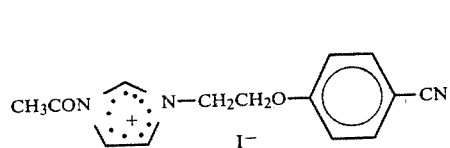
19. The imidazole derivative claimed in claim 5 of the formula:
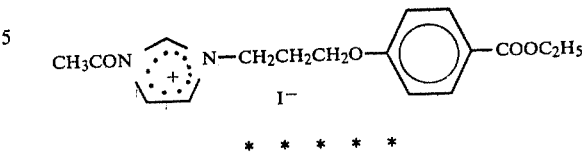
* * * * *

UNITED STATES PATENT AND TRADEMARK OFFICE
CERTIFICATE OF CORRECTION

PATENT NO. : 4,461,905
DATED : 7/24/84
INVENTOR(S) : Iizuka, Kinji, Kamijo, Tetsuhide, Yamamota, Ryoji It is certified that error appears in the above-identified patent and that said Letters Patent is hereby corrected as shown below:

Title page, after "Assignee: Ono Pharmaceutical Company, Ltd." please insert --Kissei Pharmaceutical Company, Ltd.--

Signed and Sealed this

Twenty-eighth Day of May 1985

[SEAL]

Attest:

DONALD J. QUIGG

Attesting Officer     Acting Commissioner of Patents and Trademarks